(12) United States Patent
Wallace et al.

(10) Patent No.: US 11,648,112 B2
(45) Date of Patent: May 16, 2023

(54) METHOD FOR POSITIONING A HEART VALVE

(71) Applicant: Cephea Valve Technologies, Inc., Santa Clara, CA (US)

(72) Inventors: Dan Wallace, Santa Cruz, CA (US); Aaron Grogan, Scotts Valley, CA (US)

(73) Assignee: Cephea Valve Technologies, Inc., Santa Clara, CA (US)

(*) Notice: Subject to any disclaimer, the term of this patent is extended or adjusted under 35 U.S.C. 154(b) by 353 days.

(21) Appl. No.: 16/633,384

(22) PCT Filed: Jul. 25, 2018

(86) PCT No.: PCT/US2018/043762
§ 371 (c)(1),
(2) Date: Jan. 23, 2020

(87) PCT Pub. No.: WO2019/023385
PCT Pub. Date: Jan. 31, 2019

(65) Prior Publication Data
US 2020/0229920 A1 Jul. 23, 2020

Related U.S. Application Data

(60) Provisional application No. 62/536,932, filed on Jul. 25, 2017.

(51) Int. Cl.
*A61F 2/24* (2006.01)
*A61B 34/32* (2016.01)
(Continued)

(52) U.S. Cl.
CPC .......... *A61F 2/2427* (2013.01); *A61B 6/12* (2013.01); *A61B 6/4014* (2013.01);
(Continued)

(58) Field of Classification Search
CPC ....... A61F 2/2427; A61B 6/12; A61B 6/4416; A61B 6/4417; A61B 6/4266;
(Continued)

(56) References Cited

U.S. PATENT DOCUMENTS 5,571,215 A 11/1996 Sterman et al.
8,870,948 B1 10/2014 Erzberger et al.
(Continued)

FOREIGN PATENT DOCUMENTS

CN 102824230 A 12/2012
CN 104363861 A 2/2015
(Continued)

OTHER PUBLICATIONS

International Search Report for PCT/US2018/043762 dated Oct. 11, 2018, 2 pages.
(Continued)

*Primary Examiner* — Chao Sheng
(74) *Attorney, Agent, or Firm* — Wei & Sleman LLP (57) ABSTRACT

Systems and methods for delivery a medical device to a heart valve annulus are disclosed. A method of delivering a medical device to a heart valve annulus includes: (1) aligning a first imaging sensor such that a view of the first imaging sensor is along a primary plane of the heart valve annulus; (2) aligning a second imaging sensor such that a view of the second imaging sensor is along a longitudinal axis of the heart valve annulus; (3) attaching a delivery system holding the medical device to a delivery arm; (4) adjusting the delivery arm to set an angle of the delivery system perpendicular to the primary plane using images from the first imaging sensor; (5) adjusting the delivery arm to center the delivery device in the heart valve annulus using images from the second imaging sensor; and (6) deploying the medical device into the heart valve annulus.

11 Claims, 8 Drawing Sheets

(51) Int. Cl.
  *A61B 90/00* (2016.01)
  *A61B 6/12* (2006.01)
  *A61B 6/00* (2006.01)
  *A61B 8/08* (2006.01)
  *A61B 8/00* (2006.01)
  *A61B 90/50* (2016.01)

(52) U.S. Cl.
  CPC .......... *A61B 6/4266* (2013.01); *A61B 6/4417* (2013.01); *A61B 6/4441* (2013.01); *A61B 8/0833* (2013.01); *A61B 8/4416* (2013.01); *A61B 34/32* (2016.02); *A61B 90/37* (2016.02); *A61B 2090/378* (2016.02); *A61B 2090/3764* (2016.02); *A61B 2090/508* (2016.02)

(58) Field of Classification Search
  CPC ... A61B 6/4014; A61B 6/4441; A61B 8/4416; A61B 34/32; A61B 8/0833; A61B 90/37; A61B 2090/3764; A61B 2090/378; A61B 2090/508
  See application file for complete search history.

(56) References Cited

U.S. PATENT DOCUMENTS

| | | | |
|---|---|---|---|
| 10,368,990 B2 | 8/2019 | Noe et al. | |
| 10,869,755 B2 | 12/2020 | Granada et al. | |
| 2003/0074011 A1 | 4/2003 | Gilboa et al. | |
| 2006/0293643 A1* | 12/2006 | Wallace | A61B 34/71 606/1 |
| 2008/0161830 A1* | 7/2008 | Sutherland | A61B 34/74 606/130 |
| 2009/0185657 A1* | 7/2009 | Klingenbeck-Regn | A61B 6/4417 378/14 |
| 2009/0264759 A1* | 10/2009 | Byrd | A61M 25/0136 600/445 |
| 2010/0114308 A1 | 5/2010 | Maschke | |
| 2012/0158129 A1 | 6/2012 | Duffy et al. | |
| 2014/0052241 A1 | 2/2014 | Harks et al. | |
| 2014/0107665 A1 | 4/2014 | Shellenberger et al. | |
| 2014/0128726 A1 | 5/2014 | Quill et al. | |
| 2015/0119637 A1 | 4/2015 | Alvarez et al. | |
| 2015/0142013 A1* | 5/2015 | Tanner | A61B 34/37 606/130 |
| 2015/0223773 A1 | 8/2015 | John et al. | |
| 2015/0302634 A1 | 10/2015 | Florent et al. | |
| 2016/0158000 A1 | 6/2016 | Granada et al. | |
| 2016/0206280 A1 | 7/2016 | Vidlund | |
| 2016/0220785 A1* | 8/2016 | Fabro | A61M 25/0043 |
| 2017/0119526 A1 | 5/2017 | Luong et al. | |
| 2019/0021699 A1* | 1/2019 | Bracken | A61B 8/4416 |
| 2019/0127188 A1 | 5/2019 | Stuedal et al. | |
| 2019/0374342 A1 | 12/2019 | Gregg et al. | |

FOREIGN PATENT DOCUMENTS

| | | |
|---|---|---|
| JP | 2017502709 A | 1/2017 |
| WO | 2010040215 A1 | 4/2010 |
| WO | 2010119445 | 10/2010 |
| WO | 2015061756 | 4/2015 |
| WO | 2016183523 A1 | 11/2016 |
| WO | 2016183526 A1 | 11/2016 |
| WO | 2017122109 A1 | 7/2017 |
| WO | 2017167759 A1 | 10/2017 |
| WO | 2017218877 A1 | 12/2017 |
| WO | 2018094069 A1 | 5/2018 |

OTHER PUBLICATIONS

Chinese Search Report for Application No. 201880057755.1, dated Jul. 8, 2021, 2 pages.
First Australian Examination Report for AU2018306296 dated May 18, 2020; 6 pages.
Supplementaty European Search Report for EP application No. 18839347.4 dated May 4, 2021, 4 pages.

* cited by examiner

METHOD FOR POSITIONING A HEART VALVE

CROSS-REFERENCE TO RELATED APPLICATIONS

This application is a national phase entry under 35 U.S.C. § 371 of International Application No. PCT/US2018/043762, filed on Jul. 25, 2018, which claims priority to U.S. Provisional Patent Application No. 62/536,932, filed on Jul. 25, 2017, titled "SYSTEM AND METHOD FOR POSITIONING A HEART VALVE," the disclosures of which are hereby incorporated by reference herein.

INCORPORATION BY REFERENCE

All publications and patent applications mentioned in this specification are herein incorporated by reference to the same extent as if each individual publication or patent application was specifically and individually indicated to be incorporated by reference.

BACKGROUND

The mitral valve lies between the left atrium and the left ventricle of the heart. Various diseases can affect the function of the mitral valve, including degenerative mitral valve disease and mitral valve prolapse. These diseases can cause mitral stenosis, in which the valve fails to open fully and thereby obstructs blood flow, and/or mitral insufficiency, in which the mitral valve is incompetent and blood flows passively in the wrong direction.

Many patients with heart disease, such as problems with the mitral valve, are intolerant of the trauma associated with open-heart surgery. Age or advanced illness may have impaired the patient's ability to recover from the injury of an open-heart procedure. Additionally, the high costs associated with open-heart surgery and extra-corporeal perfusion can make such procedures prohibitive.

Patients in need of cardiac valve repair or cardiac valve replacement can be served by minimally invasive surgical techniques. In many minimally invasive procedures, small devices are manipulated within the patient's body under visualization from a live imaging source like ultrasound, fluoroscopy, or endoscopy. Minimally invasive cardiac procedures are inherently less traumatic than open procedures and may be performed without extra-corporeal perfusion, which carries a significant risk of procedural complications.

Prosthetic valve replacement procedures can be difficult, and various factors are generally taken into account when placing the valve. First, the prosthetic valve should be placed at the same or very nearly the same angle as the native valve. A valve that is off axis could cause turbulent blood flow and/or potential para-valvular leaks. Second, the prosthetic valve should ideally have concentricity. This means that the valve is placed in the same center as the native valve. An off center deployment or valve placement could affect the mechanism of neighboring valves or the heart's conductive system. Finally, the prosthetic valve should be at the proper depth within the patient's heart with respect to the location of the native valve, as otherwise, the prosthetic valve may interfere with the conductive nature of the heart as well.

However, in general, trans-catheter mitral valve delivery can be difficult because the physician must control the placement of the valve in at least three degrees of motion using at least two different imaging modalities. It is common for the user to correctly position the valve in one degree of motion, but to then lose that position while trying to obtain a correct position in a second degree of motion. Similarly, it isn't unusual for the user to lose position in an x-ray imaged degree of motion when switching to ultrasound to obtain a correct position in a second degree of motion.

A safe and efficient system and method for replacement of a cardiac valve that addresses some or all of these concerns is described herein.

SUMMARY OF THE DISCLOSURE

Described herein are mechanical positioning aids that may be used to assist a physician in placing a mitral valve in the native valve orifice. The positioning aid can maintain a first position while allowing the user to adjust a second degree of motion to obtain a second position.

In general, in one embodiment, a system for delivering a medical device to a heart valve annulus includes a first imaging sensor, a second imaging sensor, a delivery arm, and a control system. The first imaging sensor is configured to be aligned such that a view of the first imaging sensor is along a primary plane of the heart valve annulus. The second imaging sensor is configured to be aligned such that a view of the second imaging sensor is along a longitudinal axis of the heart valve annulus. The delivery arm is configured to hold a medical device delivery system. The control system is configured to adjust the delivery arm to set an angle of the delivery system perpendicular to the primary plane using images from the first imaging sensor or adjust the delivery arm to center the delivery device in the heart valve annulus using images from the second imaging sensor.

This and other embodiments can include one or more of the following features. The control system can be further configured to adjust the delivery arm to insert the delivery device along the longitudinal axis prior to deploying the medical device. The control system can be configured to adjust the delivery arm to insert the delivery device along the longitudinal axis using images from the first imaging sensor. The control system can be configured to do both steps of adjusting the delivery arm to set an angle of the delivery system perpendicular to the primary plane using images from the first imaging sensor and adjusting the delivery arm to center the delivery device in the heart valve annulus using images from the second imaging sensor. The first imaging sensor can be an x-ray sensor. The second imaging sensor can be an ultrasound sensor. The heart valve annulus can be a mitral valve annulus. The medical instrument can be a prosthetic mitral valve. The delivery arm can include at least six degrees of freedom. The control system can be further configured to create a computed pivot point for the delivery device at a center of the heart valve annulus. The control system can be further configured to allow the robotic arm to travel along a virtual rail when manually acted upon by a user.

In general, in one embodiment, a method of delivering a medical device to a heart valve annulus includes: (1) aligning a first imaging sensor such that a view of the first imaging sensor is along a primary plane of the heart valve annulus; (2) aligning a second imaging sensor such that a view of the second imaging sensor is along a longitudinal axis of the heart valve annulus; (3) attaching a delivery system holding the medical device to a delivery arm; (4) adjusting the delivery arm to set an angle of the delivery system perpendicular to the primary plane using images from the first imaging sensor; (5) adjusting the delivery arm to center the delivery device in the heart valve annulus using images from the second imaging sensor; and (6) deploying the medical device from the delivery system into the heart valve annulus.

This and other embodiments can include one or more of the following features. The method can further include adjusting the delivery arm to insert the delivery device along the longitudinal axis prior to deploying the medical device. Adjusting the delivery arm to insert the delivery device along the longitudinal axis can include using images from the first imaging sensor. Using images from the first imaging sensor can include aligning markers on the delivery device with the primary plane. The first imaging sensor can be an x-ray sensor. The method can further include inserting a coronary vein wire and injecting contrast dye to identify the mitral valve plane in images from the x-ray sensor. The second imaging sensor can be an ultrasound sensor. The heart valve annulus can be a mitral valve annulus. The medical instrument can be a prosthetic mitral valve. The delivery arm can include at least six degrees of freedom. The delivery arm can be a mechanical un-powered arm. The delivery arm can be a robotic arm. At least one of the steps of adjusting the delivery arm to set an angle or adjusting the steps of adjusting the delivery arm can be performed automatically by a control system of the robotic arm. The control system can be configured to create a computed pivot point for the delivery device at a center of the heart valve annulus. A control system of the robotic arm can be configured to allow the robotic arm to travel along a virtual rail when manually acted upon by a user.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

The valve positioning systems described herein can be used to deliver and deploy a wide variety of replacement heart valves, such as prosthetic valves adapted to be minimally invasively delivered. For example, the valve positioning systems described herein can be configured to be able to deliver and deploy a replacement heart valve, such as a mitral valve, that includes proximal and distal anchors.

Exemplary prosthetic valves that can be delivered and deployed include the expandable prosthetic valves described in application Ser. No. 14/677,320, filed Apr. 2, 2015, Publication No. US 2016-0158000 A1, titled "REPLACEMENT CARDIAC VALVES AND METHODS OF USE AND MANUFACTURE" in U.S. Pat. No. 8,870,948, and in International Patent Application No. PCT/US2016/032550, filed May 13, 2016, titled "REPLACEMENT MITRAL VALVES," in U.S. patent application Ser. No. 16/012,666, filed Jun. 19, 2018, titled "REPLACEMENT MITRAL VALVES," all of which are incorporated by reference herein.

Further, the valve positioning systems described herein can be used with the delivery devices described, for example, in International Patent Application No. PCT/US2016/032546, filed May 13, 2016, titled "CARDIAC VALVE DELIVERY DEVICES AND SYSTEMS," U.S. Provisional Patent Application No. 62/424,021, filed Nov. 18, 2016, titled "CARDIAC VALVE DELIVERY DEVICES AND SYSTEMS," U.S. Provisional Patent Application No. 62/424,051, filed Nov. 18, 2016, and titled "CARDIAC VALVE DELIVERY DEVICES AND SYSTEMS", and International Patent Application No. PCT/US2017/062045, filed Nov. 16, 2017, and titled "CARDIAC VALVE DELIVERY DEVICES AND SYSTEMS", the entireties of which are incorporated by reference herein.

A replacement heart valve, such as a mitral valve prosthesis, can be delivered using one of the valve positioning systems described herein to a cardiac valve orifice, such as the mitral valve, using minimally invasive techniques. In some embodiments, a small incision can be made in the patient's body, and the prosthesis can be passed through the apex of the heart to, for example, the mitral valve. This can be referred to as the transatrial delivery approach. In other embodiments, the prosthesis can be delivered through the venous system and into the left atrium through a transseptal puncture. A transseptal approach can impart size limitations on the delivery and thus the delivery profile of the replacement heart valve. Additionally, a transseptal approach can also impart certain flexibility requirements on the replacement heart valve. For both delivery approaches, the distal-most anchor can be delivered to the ventricle while the proximal-most anchor can be delivered to the atrium.

The valve positioning systems described herein can be used to delivery a replacement heart valve (e.g., via a delivery device) to the treatment site for deployment.

Figure 1:
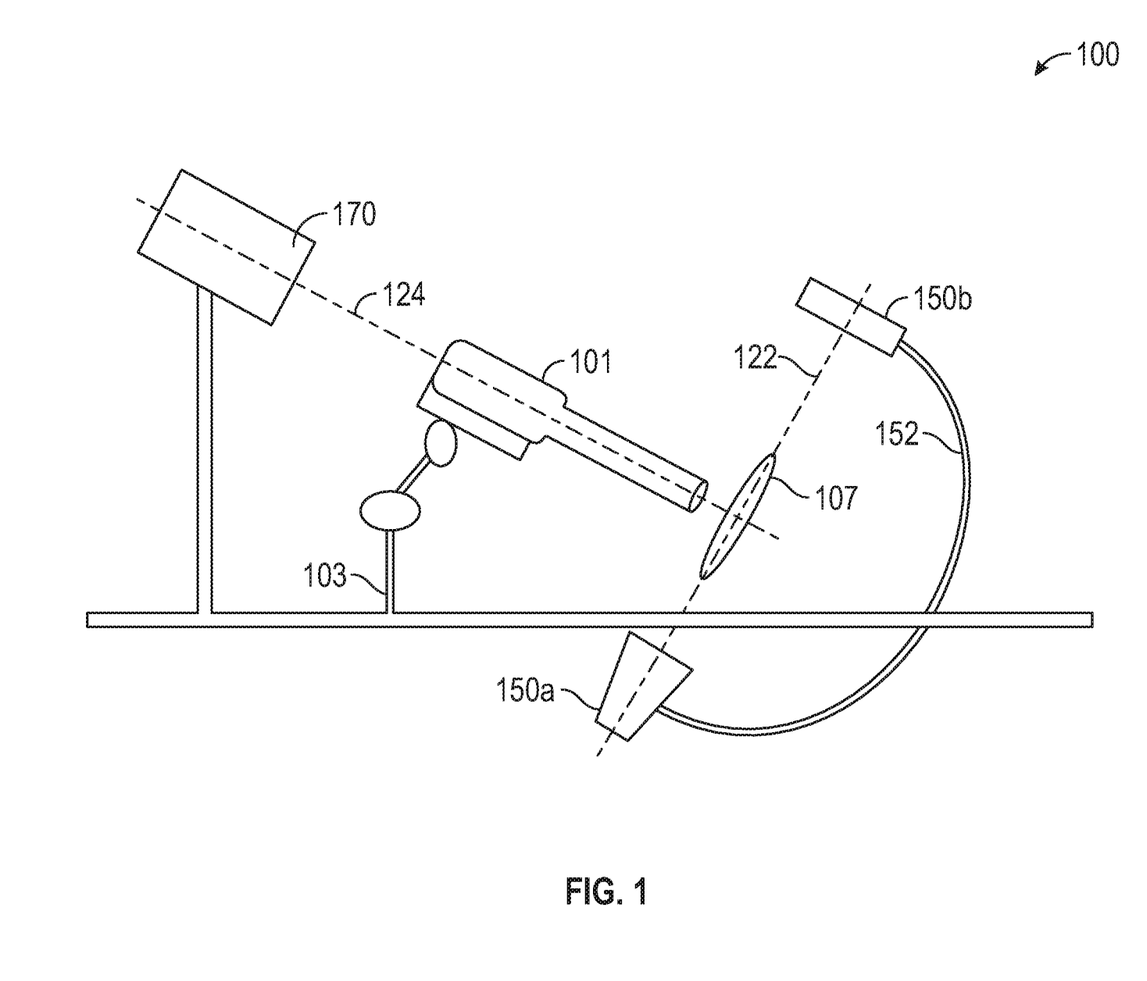
FIG. 1 shows a valve positioning system.

Referring to FIG. 1, in some embodiments, a valve positioning system 100 can include an arm 103 that is used to support a mitral valve delivery device 101 (which can be any delivery device described, for example, in International Application No. PCT/US2016/032546, filed May 13, 2016, and titled "CARDIAC VALVE DELIVERY DEVICES AND SYSTEMS", International Application No. PCT/US2017/037850, filed Jun. 16, 2017, and titled "CARDIAC VALVE DELIVERY DEVICES AND SYSTEMS", and International Application No. PCT/US2017/062045, filed Nov. 16, 2017, and titled "CARDIAC VALVE DELIVERY DEVICES AND SYSTEMS"). The valve positioning system 100 can further include two imaging modalities. The imaging modalities can be, for example, ultrasound or x-ray. Further, the two imaging modalities can be identical to one another (e.g., provide the same type of imaging) or different. As shown in FIG. 1, for example, the imaging modalities can include an ultrasound sensor 170 and an x-ray sensor 150a,b (150a is the emitter while 150b is the detector, which can be part of a c-arm 152). The x-ray sensor 150a,b can be positioned, for example, such that the x-ray image is taken down the plane 122 of the mitral valve 107 (i.e., on-edge with the plane 122 of the mitral valve). This position of the x-ray sensor 150a,b can allow orientation of the delivery device 101 (and thus the mitral valve) orthogonal to the native valve 107. Further, the ultrasound sensor 170 can be positioned, for example, such that the ultrasound image is taken down the longitudinal axis 124 of the valve 107 (i.e., the axis that extends through the center of the valve 107). This position of the ultrasound sensor 170 can allow positioning of the delivery device 101 (and thus the mitral valve) in the center of the native valve 107.

Figure 2:
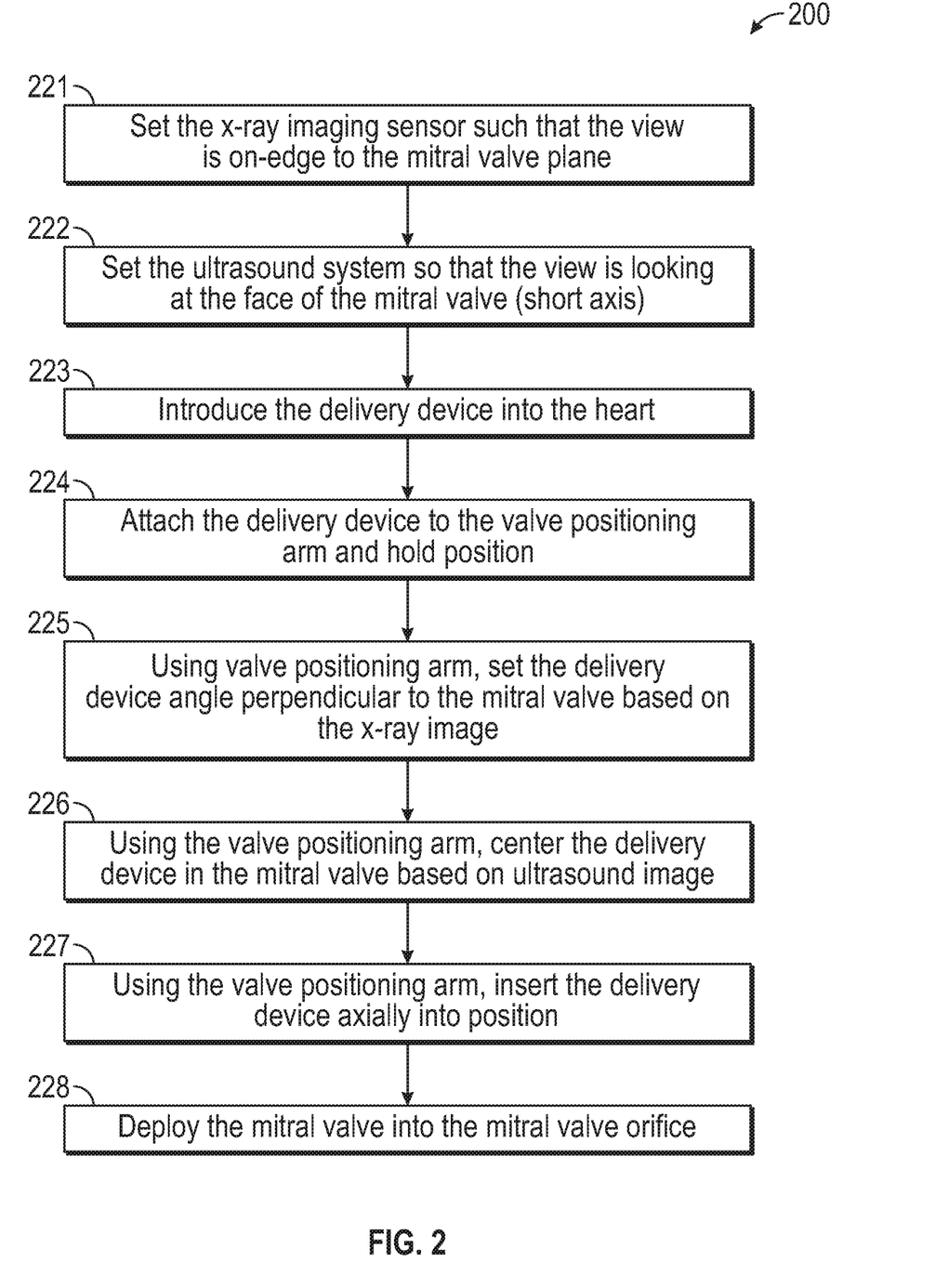
FIG. 2 is a flow chart of the method of delivering a mitral valve using a valve positioning system.

A method of delivering a mitral valve to the mitral valve orifice using the valve positioning system of FIG. 1 is shown in the flow chart 200 of FIG. 2. To begin, at step 221, the first imaging modality (e.g., x-ray imaging sensor 150a,b) is maneuvered so as to have a set relationship with the native mitral valve 107 of the patient. For example, the position of the x-ray emitter 150a can be set such that the view of the x-ray imaging sensor 150a,b is on-edge to the plane 122 of the native mitral valve 107. In some embodiments, contrast injections and a coronary vein wire can be used to better visualize the plane 122 of the mitral valve 107 under x-ray (and thus to provide for placement of the x-ray emitter 150a with increased accuracy). When contrast injections and a coronary vein wire are to be used, the coronary vein wire can be placed in the coronary sinus, which is positioned in the body along the same plane 122 as the native mitral valve 107. After placing the wire in the coronary sinus, contrast can be provided by injecting radio-opaque dye into the ventricle underneath the mitral annulus. The contrast injection can circle under the annular plane, creating a semicircular ring that is visible immediately underneath the mitral valve and parallel to the plane 122 of the mitral valve annulus. The image plane of the x-ray system 150a,b can then be rotated so as to be perpendicular to the mitral valve plane 122 (i.e., by making the ring of dye appear to be as flat as possible in the x-ray image). The final position of the x-ray emitter 150a will advantageously be relative to, and within, the coordinate system of the mitral valve 107. An exemplary position of the emitter 150a after the emitter 150a has been positioned within the mitral valve coordinate system is, for example, is LAO 16° Cranial 4° where LAO is a "Left Anterior Oblique" angle measured relative to the patient and floor in the patient's left hand to right hand direction and Cranial is measured in the direction of the patient's head in a head to foot direction.

At step 222, the second imaging modality (e.g., ultrasound system 170) is set such that the view is looking at the face of the mitral valve (i.e., along the axis 124). For example, a para-sternal short-axis view at the level of the mitral valve can be used. If a second x-ray system is used as the second imaging modality rather than the ultrasound system 170, the second x-ray system can be positioned using the contrast injections and coronary vein wire as described above. The second the x-ray system may be moved into a position to be parallel to the mitral plane by rotating the x-ray system 150a,b until the footprint of the dye ring image is maximized in a circular perspective.

At step 223, the delivery device 101 is positioned into the heart (e.g., through an atrial purse-string) such that the replacement mitral valve is approximately at the location of the native mitral valve orifice 107.

At step 224, the delivery device 101 is attached to the positioning arm 103.

Figure 3A:
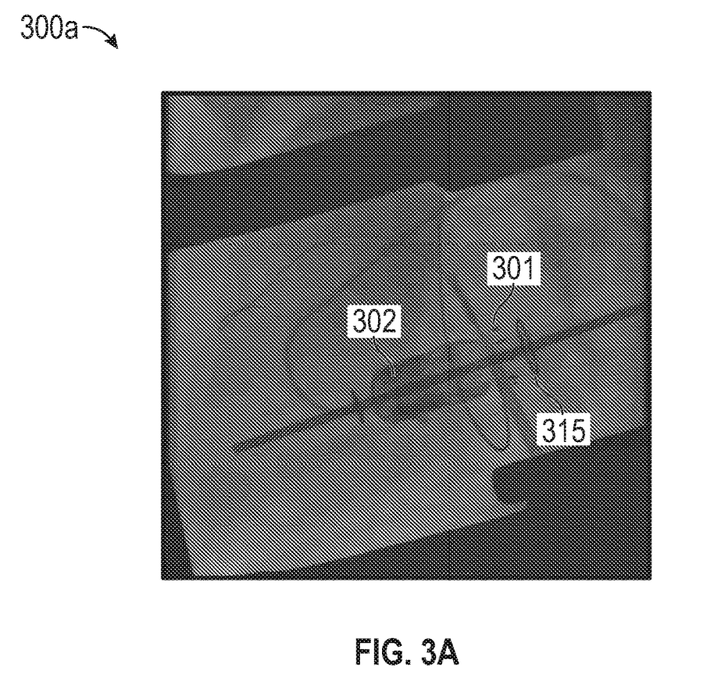
FIG. 3A shows a delivery device with a mitral valve therein where the delivery device is not orthogonal to the native mitral valve orifice.
Figure 3B:
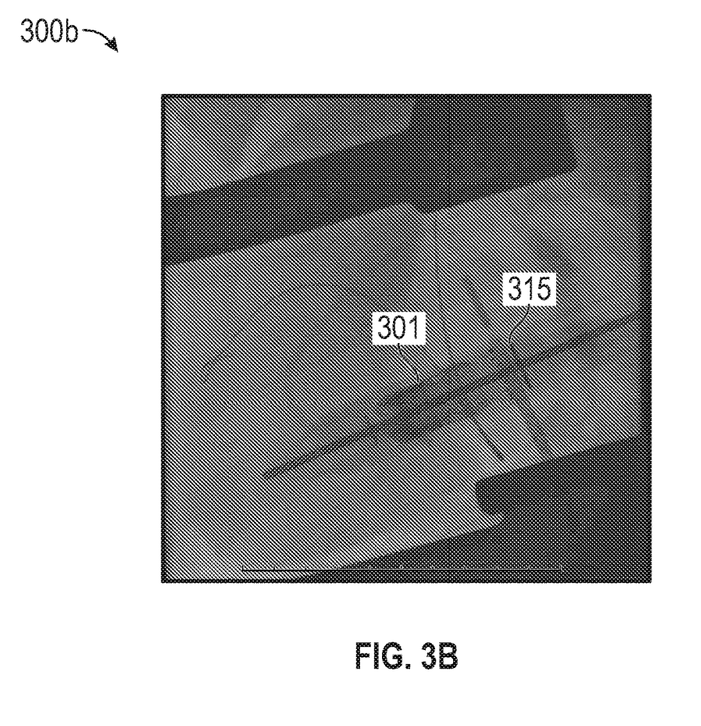
FIG. 3B shows a delivery device housing a mitral valve where the delivery device is orthogonal to the native mitral valve.

At step 225, the positioning arm 103 is used to set the angle of the delivery device 101 such that it is perpendicular to the plane 122 of the native valve 107 based upon the image from the first imaging modality (e.g., the x-ray sensor 150a,b). Thus, the delivery device 101 can be pivoted until it is orthogonal to the plane 122. In some embodiments, the orthogonal position can be confirmed because circumferential rings (e.g., made of tantalum wire) on the delivery device 101 can appear to be a closed, single line rather than an open oval or circle in the image from the first imaging modality (e.g., the x-ray sensor 150a,b) that is aligned with the mitral valve plane 122. For example, FIG. 3A shows an x-ray image 300a of a delivery device 301 housing a mitral valve 302. The delivery device 301 is not orthogonal to the native mitral valve orifice, as is indicated by the oval-shaped tantalum wire 315 in the x-ray image 300a. In contrast, FIG. 3B shows an x-ray image 300b in which the delivery device 301 is orthogonal to the native mitral valve, as is indicated by the line of tantalum wire 315 in the 300b.

Figure 4:
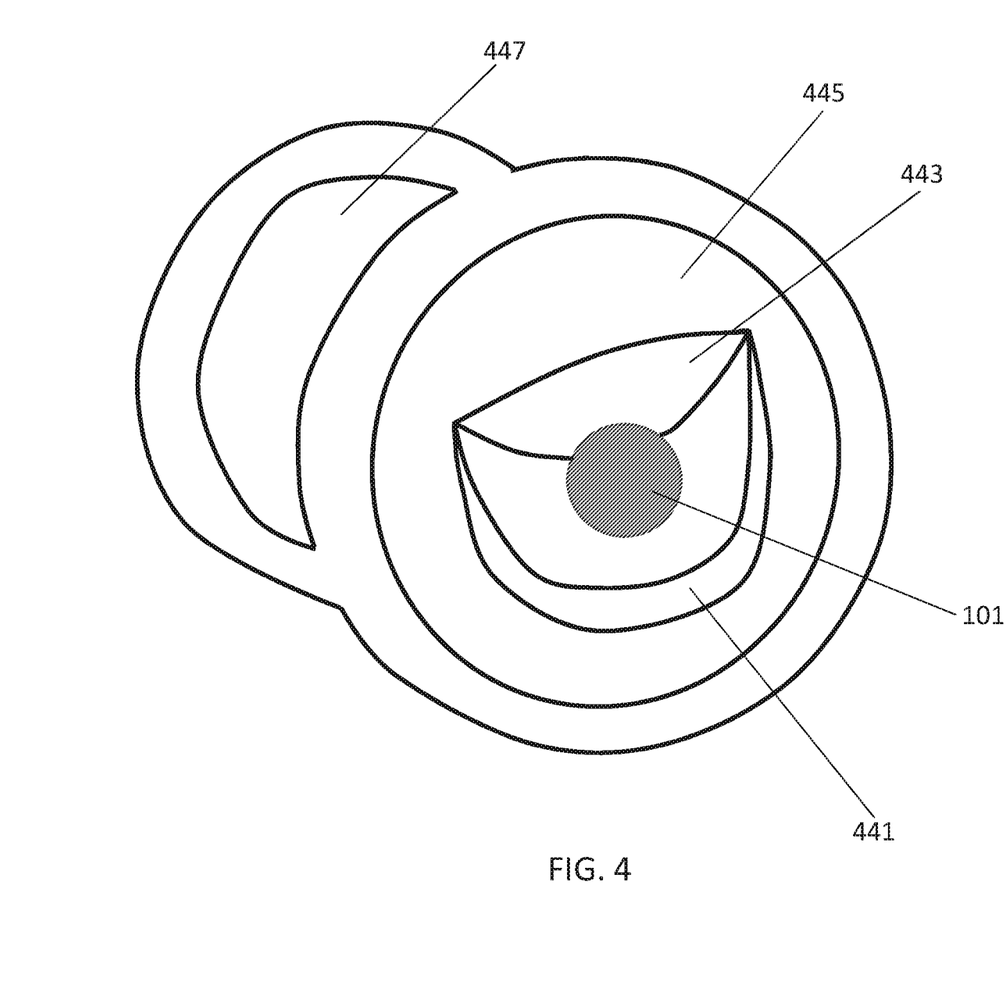
FIG. 4 shows a delivery device with a mitral valve therein where the delivery device is centered in the mitral valve annulus.

At step 226, the positioning arm 103 is used to center the delivery device 101 in the native mitral valve annulus based on the ultrasound image. For example, FIG. 4 shows the delivery device 101 centered in the annulus between the anterior mitral valve leaflet 443 and the posterior mitral valve leaflet 441. The left ventricular outflow tract 445 and the right ventricle 447 can also be seen.

Figure 5A:
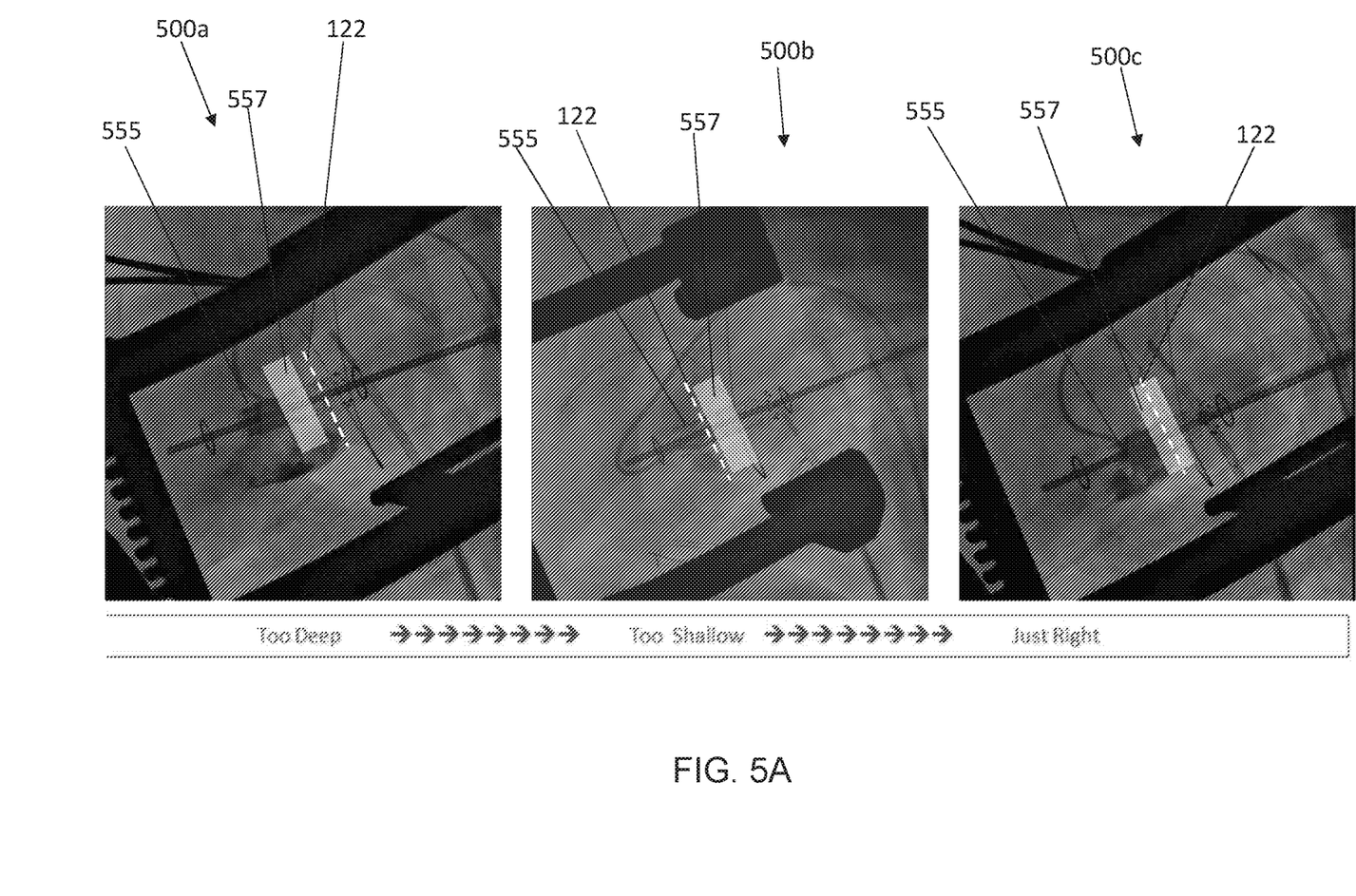
FIG. 5A shows a delivery device with a mitral valve therein where the delivery device is aligned with the mitral valve plane.
Figure 5B:
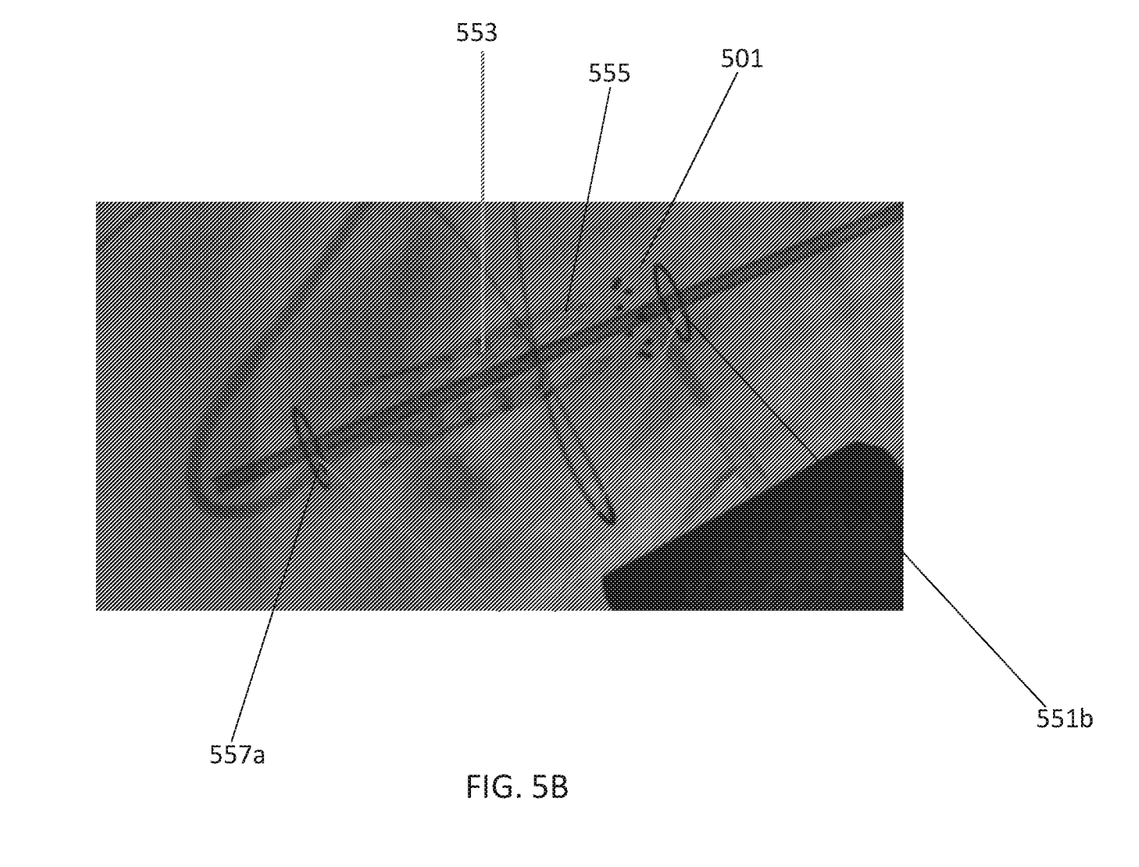
FIG. 5B shows a close up of the delivery device and valve of FIG. 5A.

At step 227, the depth of insertion of the delivery device 103 is set using the positioning arm 103. In some embodiments, the x-ray image can be used to set the depth by aligning markers on the delivery device with the mitral plane 122. For example, FIG. 5A shows x-ray images 500a, 500b, and 500c. The x-ray image 500a shows that the waist 557 of the mitral valve replacement 555 is below the mitral valve plane 122. The x-ray image 500b shows that the waist 557 of the mitral valve replacement 555 is above the mitral valve plane 122. Finally, x-ray image 500c shows that the waist 557 of the mitral valve replacement 555 is aligned with the mitral valve plane 122. FIG. 5B shows markers 551a,b (e.g., rings) on the delivery device 501 and markers 553 on the valve replacement 555 that can be used to align the delivery device with the mitral plane 122.

Once the depth, angle, and centrality of the mitral valve have been set, then the valve can be deployed (at step 228).

Figure 6:
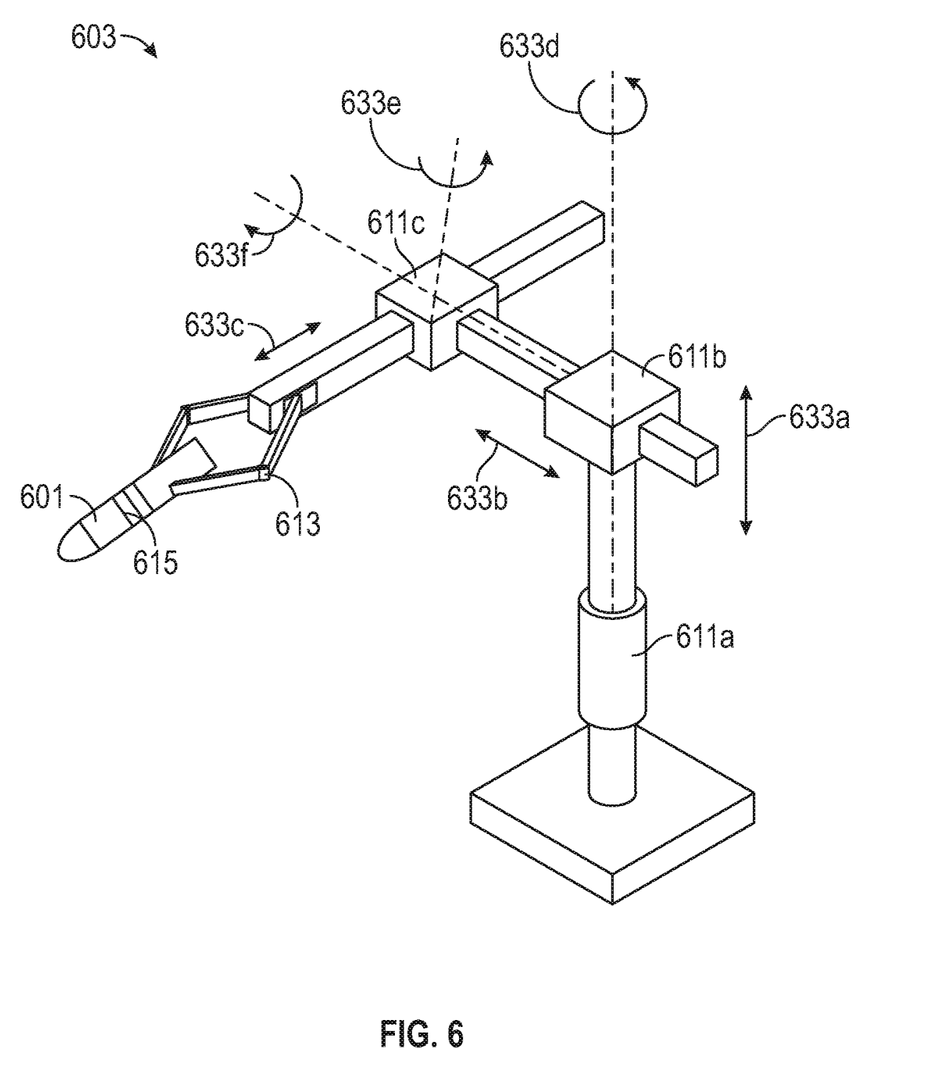
FIG. 6 shows a mechanical valve positioning arm.

Referring to FIG. 6, in some embodiments, the positioning arm used herein can be a mechanical un-powered arm 603 having an attachment mechanism 613 configured to hold the delivery device 601 and a plurality of locks or brakes 611a-d configured to control the position of the delivery device 601. The arm 603 can include, for example, mechanical locks configured to control the degrees of freedom of the device (i.e., the angular, rotational, and/or axial positions of the delivery device. The positioning arm 603 can include six degrees of freedom (shown by arrows 633a-f).

In one embodiment, following the steps of the flow chart 200 when using the positioning arm 603, the brake 611d can be released to pivot the delivery device 601 to the orthogonal position, e.g., using the rings 615 as they appear in the x-ray image (for step 225). Once the delivery device 601 is at the correct orthogonal position, the brake 611d can be locked again. Further, brakes 611a and/or 611b can be released to allow the delivery device 601 to be centered (per step 226), and then the brakes 611a and/or 611b can be locked in place. Finally, with the first two positions held in place by the brakes 611a,b, and d, the user can unlock the brake 611c to allow the insertion depth to be set (at step 227).

Figure 7:
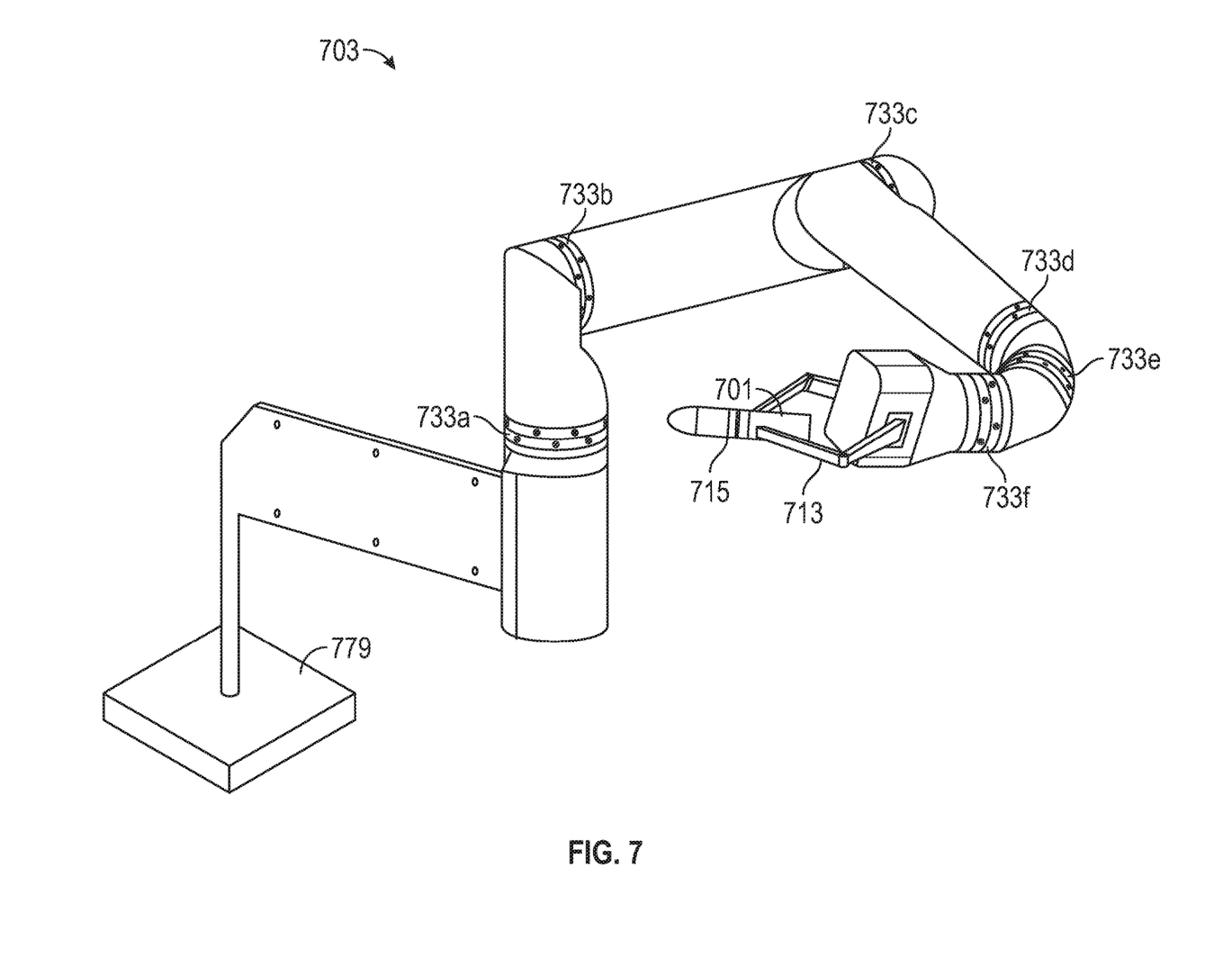
FIG. 7 shows a robotic valve positioning arm.

Referring to FIG. 7, in some embodiments, the valve positioning arm used herein can be a computer controlled, servo-mechanical robotic arm 703. The arm 703 can include a base 779 and a mount 713 configured to mount the delivery device 701 thereto. In some embodiments, the arm 703 can have five to seven degrees of freedom for positioning the mitral valve delivery system. For example, arm 703 includes six movable (e.g., motorized) connections or joints 777a-f that provide six degrees of freedom. An additional degree of freedom can be provided (e.g., to avoid collisions with other objects during use). Further, the arm 703 can include or be connected to a control system configured to move the robotic arm 703.

In one embodiment, the robotic arm 703 can include a 6 degree of freedom (DOF) force sensor mounted at or near the distal end of the arm 703. The user can thus hold the robot 703, and control software in or connected to the robotic arm 703 can use information from the force sensor to follow the user's input and move the robotic arm 703 (and thus the delivery device 701). In one specific example, the force sensor(s) can be placed on or into the distal section of the robotic arm 703. The force sensor(s) can provide input into the robotic control systems to move multiple degrees of freedom in pre-programmed sequence. In such an example, the user can grasp the robotic arm 703 near the distal end and make a motion as of insertion. The force sensor(s) can then sense the applied force and direction, and the robotic control system can send output signal to the motors in the joints 777a-f such that the joints 777a-f can rotate in concert to affect a straight-line movement.

In another embodiment, the robotic arm 703 can include a user interface (button, GUI, voice control) on or connected thereto that can be in communication with the robotic control system. Further, the robotic arm 703 can include an actuator (e.g., button) on or connected thereto. In use, the user can actuate the actuator to "clutch" the robotic arm 703 into an "impedance" mode or "following" mode. The user can then position the robot arm 703 so that the tip of the delivery device 701 is just touching the surface of the heart. At this position, the user can input the position of the delivery device 701 (e.g., a "ready" position) into the user interface. The control system can then create a computed center or pivot point at the surface of the heart. This information may be used to reduce side-to-side motion at the surface of the heart to reduce the chance of trauma at the insertion point of the delivery device 701. Because the tip of the delivery device 701 is in a rigid, encoded joint chain from the base of the robot arm 703 to the heart, touching the surface of the heart informs the robotic control system of the position of the insertion point relative to the robotic coordinate system at the base of the robotic system. When the system has knowledge of the insertion point, the system may treat that point as a pivot or remote center where the only motions of the delivery system 701 allowed are rotations and depth insertion (i.e., no side-to-side motions are allowed that may traumatize the insertion point are initiated by the system).

In one embodiment, to control the pivoted position of the robotic arm 703 (i.e., such that the delivery device 701 is orthogonal to the plane 122 of the mitral valve orifice as at step 225), the user can input the angles of the first imaging modality (e.g., the x-ray sensor 150a,b) into the control system for the robotic arm 703 when the first imaging modality is set such that the view is on-edge to the mitral plane 122. Using the image (e.g., x-ray data), the robotic arm 703 can automatically position the delivery device 701 perpendicular to the plane 122 of the native mitral valve 107. In another embodiment, the user can position the x-ray arm 703 manually (or through controlled movement with a user interface) such that the delivery device 701 is perpendicular to the native valve 107 based on the image, e.g., such that the rings 715 on the delivery device are closed as described above.

To ensure that the mitral valve replacement is positioned properly within the center of the native orifice (as at step 226), the robotic arm 703 can be switched to a mode that allows the delivery device to be centered in the mitral valve using the second imaging modality (e.g., ultrasound). In this mode, the robotic arm can become a "virtual stir" that maintains the depth and orthogonality of the delivery device while allowing the user to adjust the centering of the delivery device.

To control the insertion depth (as at step 227), the user can make an input to the robotic control system of the robotic arm 703 that places the arm 703 in a mode where the delivery device is allowed to move along a "virtual rail." In other words, the user may hold the distal point of the robotic arm 703, and the arm 703 can follow the user's input to move in or out along an insertion axis orthogonal to the native mitral valve. In this "virtual rail" mode, the control system of the robotic arm 703 may be set to allow zero motion in directions other than the direction of insertion. Alternatively, the "virtual rail" may provide almost no resistance in the direction of insertion while providing some greater resistance to motion in directions other than insertion. In either case, if the user is not holding onto the robot arm 703 at the distal position, the robot arm 703 can lock and hold position. While the virtual rail is set, the insertion depth can be controlled based on the first imaging modality (e.g., the image from the x-ray sensor).

In some embodiments, as the prosthetic valve is deployed from the delivery device, the user may wish to place the robotic arm 703 in a mode that allows the valve to be tensioned on the native tissue. This tension mode may be a "virtual rail" where the robot allows the user to move the delivery device 701 only in the insertion axis, or it may be an active tensioning mode where the robotic control system uses information from force sensors to apply a constant, low force in the insertion axis to keep the valve in contact with tissue as it is deployed.

In another embodiment, all motions may be controlled robotically rather than having some motions of the robotic arm 703 controlled manually. In this mode, for example, the user cam use a joystick-style input to remotely position the delivery device following the same steps. The robot arm 703 can use force sensor information to limit applied forces to reasonable levels, for example three Newtons.

The robotic arm 703 can be, for example, any of the robotic arms or systems described in International Patent Publication No. WO 2010/040215, titled "PORTABLE ROBOTIC ARM," filed Oct. 6, 2009, the entirety of which is incorporated by reference herein.

Although described for use with a mitral valve prosthetic, the systems and methods described herein can be used with a variety of different implantable devices, including stents or other valve prosthetics.

It should be understood that any elements described herein with respect to one embodiment can be substituted or combined with elements of any other embodiment(s).

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of delivering a medical device to a heart valve annulus comprising:
   orienting a first imaging sensor to obtain an on-edge image of the heart valve annulus, the on-edge image having a dimension in a direction perpendicular to a primary plane of the heart valve annulus;
   aligning the first imaging sensor based on the on-edge image such that a view of the first imaging sensor is along the primary plane of the heart valve annulus and the dimension of the on-edge image in the direction perpendicular to the primary plane of the heart valve annulus is a minimum;
   aligning a second imaging sensor such that a view of the second imaging sensor is along a longitudinal axis of the heart valve annulus;
   attaching a delivery system holding the medical device to a delivery arm;
   adjusting the delivery arm to set an angle of the delivery system, during delivery of the medical device to the heart valve annulus, perpendicular to the primary plane using images from the first imaging sensor;

adjusting the delivery arm to center the delivery system, during delivery of the medical device to the heart valve annulus, in the heart valve annulus using images from the second imaging sensor; and deploying the medical device from the delivery system into the heart valve annulus.

2. The method of claim 1, wherein the second imaging sensor is an ultrasound sensor.

3. The method of claim 1, wherein the delivery arm is a robotic arm, and a control system of the robotic arm is configured to allow the robotic arm to travel along a virtual rail when manually acted upon by a user.

4. The method of claim 1, further comprising adjusting the delivery arm to insert the delivery system along the longitudinal axis prior to deploying the medical device.

5. The method of claim 4, wherein adjusting the delivery arm to insert the delivery system along the longitudinal axis uses images from the first imaging sensor.

6. The method of claim 5, wherein using images from the first imaging sensor comprises aligning markers on the delivery system with the primary plane.

7. The method of claim 1, wherein the first imaging sensor is an x-ray sensor.

8. The method of claim 7, wherein the heart valve annulus is the mitral valve annulus, the method further comprising inserting a coronary vein wire and injecting contrast dye to identify the primary plane of the mitral valve annulus in images from the x-ray sensor.

9. The method of claim 1, wherein the delivery arm is a robotic arm.

10. The method of claim 9, wherein at least one of the steps of adjusting the delivery arm to set an angle of the delivery system or adjusting the delivery arm to center the delivery system is performed automatically by a control system of the robotic arm.

11. The method of claim 10, wherein the control system is configured to create a computed pivot point for the delivery system at a center of the heart valve annulus.

* * * * *